United States Patent [19]

Mason et al.

[11] 4,427,598
[45] Jan. 24, 1984

[54] PROCESS FOR PREPARING CYCLOPROPANE CARBOXYLIC ACID ESTER DERIVATIVES

[75] Inventors: Ronald F. Mason; Derek A. Wood, both of Kent, England

[73] Assignee: Shell Internationale Research Maatschappij B. V., Netherlands

[21] Appl. No.: 252,891

[22] Filed: Apr. 10, 1981

[30] Foreign Application Priority Data

Apr. 23, 1980 [GB] United Kingdom ............... 8013308

[51] Int. Cl.$^3$ ........................................... C07C 121/75
[52] U.S. Cl. ................. 260/465 D; 424/304
[58] Field of Search ..................... 260/465 D

[56] References Cited

U.S. PATENT DOCUMENTS

| | | | |
|---|---|---|---|
| 4,024,163 | 5/1977 | Elliott et al. | 260/347.4 |
| 4,133,826 | 1/1979 | Warnant et al. | 260/465 D |
| 4,136,195 | 1/1979 | Warnant et al. | 424/304 |
| 4,151,195 | 4/1979 | Warnant et al. | 260/465 D |
| 4,176,195 | 11/1979 | Stoutamire | 260/465 D |
| 4,260,633 | 4/1981 | Anderson et al. | 424/304 |
| 4,261,921 | 4/1981 | Smeltz | 260/465 D |

FOREIGN PATENT DOCUMENTS 1413491 11/1975 United Kingdom .

OTHER PUBLICATIONS

M. Elliott et al., "Synthetic Insecticide with a New Order of Activity", Nature, vol. 248, pp. 710–711, Apr. 19, 1974.

Itaya et al., "Synthetic Pyrethroids", A.C.S. Symposium Series 42, pp. 45–54, (1977).

*Primary Examiner*—Ethel G. Love

*Attorney, Agent, or Firm*—Pravel, Gambrell, Hewitt, Kirk & Kimball

[57] ABSTRACT

This invention relates to the preparation of cyclopropane carboxylic acid ester derivatives, which are useful as pesticides.

There is provided a process for preparing a 1:1 mixture of 1R cis S- and 1S cis R- isomers substantially free of 1S cis S- and 1R cis R- isomers of a compound of formula:

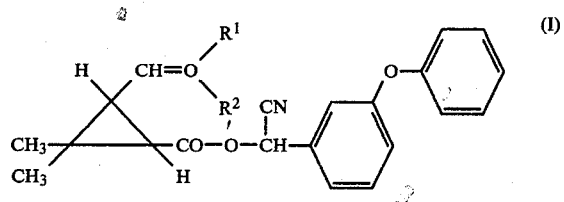

wherein $R^1$ and $R^2$ are each independently selected from chlorine, bromine and methyl, which process comprises dissolving a mixture of 1S cis S- and 1R cis R- isomers of the compound of formula I, alone or in the presence of 1R cis S- and 1S cis R-isomers, in organic amine base containing from 5 to 7 carbon atoms and being a secondary amine containing two branched alkyl groups or a tertiary amine, and crystallizing out from the resulting solution of cis - isomers of formula I in the organic amine base a 1:1 mixture of the 1R cis S- and 1S cis R- isomers substantially free of 1S cis S- and 1R cis R- isomers.

The process of the invention yields a product which contains substantially twice as much of the most active isomer of the compound of formula I as a racemic mixture of all four cis - isomers, and is a readily effected process which does not involve any asymmetric synthesis or optical resolution steps.

14 Claims, No Drawings

PROCESS FOR PREPARING CYCLOPROPANE CARBOXYLIC ACID ESTER DERIVATIVES

This invention relates to the preparation of pesticidal cyclopropane carboxylic acid ester derivatives.

Cyclopropane carboxylic acid ester derivatives of general formula

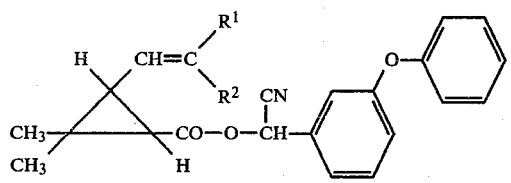

wherein $R^1$ and $R^2$ are independently selected from chlorine, bromine and methyl, are known compounds having pesticidal activity, see for example U.K. Patent Specification No. 1,413,491 or U.S. Pat. No. 4,024,163. These derivatives are members of a class of pesticidal compounds commonly referred to in the art as "pyrethroid insecticides". Compounds of formula I contain two centres of asymmetry in the cyclopropane ring of the acid moiety and a third centre of asymmetry in the alcohol moiety, leading to the existence of eight possible isomers. In general, superior pesticidal activity resides among the compounds having cis-configuration about the cyclopropane ring, as disclosed by Itaya et al in "Synthetic Pyrethroids", ACS Symposium Series 42, Pages 45 to 54, and the isomer which has the greatest pesticidal activity is generally that isomer which is conveniently designated the 1R cis S-isomer, 1R cis-designating configuration in the acid moiety and S-designating configuration in the alcohol moiety, as described by Elliott et al in Nature, Vol. 248, Pages 710 and 711 (1974).

Attempts to produce 1R cis S-single isomers rest either on synthesis routes which inherently produce intermediates containing the cyclopropane carboxylic acid moiety in exclusively 1R cis-configuration or on a route which involves an optical resolution step to separate 1R cis-compounds from 1S cis-compounds. Esterification of a 1R cis-intermediate to produce a derivative of formula I above leads to production of a mixture of 1R cis R- and 1R cis S-end products. Separation of these end products is possible by physical methods, at least in theory, since the 1R cis R- and 1R cis S-compounds are not enantiomers. However, although such separation of 1R cis R and 1R cis S-compounds has proved to be relatively readily attainable when $R^1$ and $R^2$ are both bromine atoms, it has proved to be more difficult and more costly in other cases, for example when $R^1$ and $R^2$ are both chlorine atoms.

Copending U.K. patent application No. 8037693 (Applicants' reference K 1801) describes and claims a compound of formula I in the form of a 1:1 mixture of the 1R cis S- and 1S cis R-isomers substantially free of 1S cis S- and 1R cis R-isomers. Such a compound contains, weight for weight, up to four times as much of the most pesticidally active (1R cis S-) isomer of a compound of formula I as a compound containing equal weights of all eight isomers of formula I.

According to the present invention, there is provided a process for preparing a 1:1 mixture of 1R cis S- and 1S cis R-isomers substantially free of 1S cis S- and 1R cis R-isomers of a compound of formula

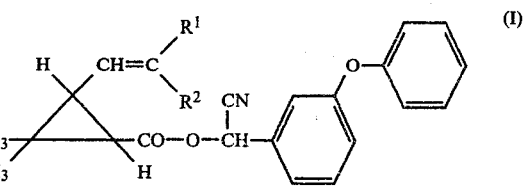

wherein $R^1$ and $R^2$ are each independently selected from chlorine, bromine and methyl, which process comprises dissolving a mixture of 1S cis S- and 1R cis R-isomers of the compound of formula I, alone or in the presence of 1R cis S- and 1S cis R-isomers, in an organic amine base containing from 5 to 7 carbon atoms and being a secondary amine containing two branched alkyl groups or a tertiary amine, and crystallising out from a resulting solution of cis-isomers of formula I in the organic amine base a 1:1 mixture of the 1R cis S- and 1S cis R-isomers substantially free of 1S cis S- and 1R cis R-isomers.

It is preferred that $R^1$ and $R^2$ are both chlorine or bromine atoms, and they are preferably both chlorine atoms.

The organic amine base causes racemisation to take place at the α-carbon atom of the alcohol moiety of the compound of formula I, so that the mixture of cis-isomers of formula I in solution in the organic amine base tends to become a racemic solution of all four cis-isomers, i.e. a solution containing equal quantities of 1R cis S-, 1S cis S-, 1R cis R- and 1S cis R-isomers, assuming that the initial mixture was optically inactive.

The Applicants have made the surprising discovery that the organic amine bases which are capable of use in the process of the invention not only have the property of causing racemisation at the α-carbon atom of the alcohol moiety of the compound of formula I but are also solvents in which the 1R cis S-/1S cis R-enantiomer pair of the isomers of formula I is substantially less soluble than the 1S cis S-/1R cis R-enantiomer pair.

In the process of the invention, as the 1:1 mixture of the 1R cis S- and 1S cis R-isomers crystallises out from the solution of cis-isomers, the solution tends to become relatively depleted in 1R cis S- and 1S cis R-isomers. This tendency is counter-balanced by the effect of the organic amine base in causing the mixture of cis-isomers to tend to become a racemic mixture of all four cis-isomers. Thus as the 1:1 mixture of 1R cis S- and 1S cis R-isomers is removed from solution by crystallisation, further quantities of the 1R cis S- and 1S cis R-isomers are formed by racemisation. This process continues until some further action is taken, e.g. removal of the crystallised 1:1 mixture of 1R cis S- and 1S cis R-isomers, for example by filtration, or until a final equilibrium is attained.

The preferred organic amine bases contain six carbon atoms. Triethylamine and disopropylamine have been found to be very effective organic amine bases. Of these, triethylamine is particularly preferred.

Although the presence of small amounts of water in the organic amine base may be tolerated, the amount of water should be less than 2% by weight of the base, advantageously less than 1%, more advantageously less than 0.5%, and the dissolution in the organic amine base and crystallisation from the resulting solution are preferably effected under substantially anhydrous conditions.

When the starting material is partly or wholly crystalline, in order to ensure complete dissolution of the 1S cis S- and 1R cis R-isomers of the compound of formula I, it is preferred to dissolve the mixture of isomers of formula I in the organic amine base at elevated temperature, e.g. a temperature in the range 50° to 80° C., conveniently 60° to 70° C. If desired the resulting solution may be filtered in order to ensure the absence of any solid particles in the solution prior to crystallisation. However, when the starting material is in the form of an oil, e.g. in the use of a freshly prepared racemic mixture of cis-isomers, the mixture of isomers of formula I is advantageously dissolved in the organic amine base at ambient temperature.

Crystallisation may advantageously be effected at ambient temperature or below, and, where elevated temperatures have been employed in order to bring the mixture of cis-isomers into solution in the organic amine base, crystallisation is preferably effected by cooling the solution to ambient temperature or below. The optimum temperatures for crystallisation will be dependent, at least in part, on the concentrations of the cis-isomers of the compound of formula I in the solution, as will be readily understood by those skilled in the art, but in general will be in the range 0° to 20° C. Conveniently, crystallisation is initiated by seeding with a few crystals of 1:1 mixture of the 1R cis S- and 1S cis R-isomers of the compound of formula I.

Recovery of the crystalline 1:1 mixture of the 1R cis S- and 1S cis R-isomers from the supernatant solution may be effected by methods such as filtration, centrifugation or decantation.

The remaining solution may then be concentrated and further crystallisation effected from the concentrated solution, or additional amounts of the cis-isomers of the compound of formula I may be dissolved in it and crystallisation effected from the resulting solution.

It will readily be appreciated that the most readily available starting material for the process of the invention will be a racemic mixture of all four cis-isomers of the compound of formula I, although the process is equally applicable to starting materials containing unequal mixtures of cis-isomers. Thus the process of the invention has the advantages that it yields a product which contains a high proportion of the most pesticidally-active isomer of the relevant compound of formula I and that it does not involve any asymmetric synthesis or optical resolution steps.

The invention also extends to the 1:1 mixture of 1R cis S- and 1S cis R-isomers of a compound of formula I substantially free of 1S cis S- and 1R cis R-isomers whenever prepared by the process of the invention, to a pesticidal composition comprising the said mixture in association with a suitable carrier therefor, and to a method of combating pests at a locus which comprises applying to the locus an effective amount of the said mixture or a composition containing the said mixture. The constitution of suitable pesticidal compositions is described in the aforementioned U.K. Patent Specification No. 1,413,491.

The invention will be further understood from the following examples, of which Examples 1 to 5, and 7 were carried out under substantially anhydrous conditions, the water content of the triethylamine being 0.1% w/w.

EXAMPLE 1

5.8 g of a crystallised racemic mixture of cis-isomers of α-cyano-3-phenoxybenzyl 3-(2,2-dichlorovinyl)-2,2-dimethylcyclopropane carboxylate (mp 58°–77° C.) was dissolved in 10 ml of triethylamine with heating to 70° C. The solution was allowed to cool to ambient temperature with stirring and was seeded with a few crystals of a 1:1 mixture of 1R cis S- and 1S cis R-isomers of α-cyano-3-phenoxybenzyl 3-(2,2-dichlorovinyl)-2,2-dimethylcyclopropane carboxylate. The precipitate which crystallised out was separated off and dried to give 3.4 g of colourless crystals mp 80°–83° C. which were shown by high performance liquid chromatography to contain 94% by weight of a 1:1 mixture of the 1R cis S- and 1S cis R-isomers of the starting material.

Concentration of the filtrate to half its volume followed by crystallisation, as above, gave a further 1.3 g of colourless crystals mp 82°–84° C. which were shown by high performance liquid chromatography to contain greater than 94% by weight of a 1:1 mixture of the 1R cis S- and 1S cis R-isomers.

Similar analysis of the triethylamine solution remaining after the second crystallisation showed the ratio of the concentrations of the 1S cis S- and 1R cis R-isomers to those of the 1R cis S- and 1S cis R-isomers to be about 16:9.

Thus in two treatment steps a 94% pure 1:1 mixture of 1R cis S- and 1S cis R-isomers of the starting material was obtained in 81% yield.

EXAMPLE 2

106 g of a mixture of cis-isomers of α-cyano-3-phenoxybenzyl 3-(2,2-dichlorovinyl)-2,2-dimethylcyclopropane carboxylate containing 42% by weight of the 1S cis S- and 1R cis R-isomers and 58% by weight of the 1R cis S- and 1S cis R-isomers was dissolved in 212 ml of triethylamine with stirring and heating to 70° C. The solution was allowed to cool with stirring and at 30° C. was seeded with a few crystals of a 1:1 mixture of 1R cis S- and 1S cis R-isomers of α-cyano-3-phenoxybenzyl 3-(2,2-dichlorovinyl)-2,2-dimethylcyclopropane carboxylate. Stirring was continued and after 58 hours, having reached an end temperature of 21° C., the solid material which had separated out was filtered off, sucked dry, and further dried in a vacuum oven at 55° C. to give 72.9 g of crystalline product, mp 82°–84° C., which was shown by high performance liquid chromatography to contain 95% by weight of a 1:1 mixture of the 1R cis S- and 1S cis R-isomers of the starting material.

The filtrate was concentrated to 70 ml, heated to 70° C. and allowed to cool with stirring and seeding followed by isolation of solid material as above, yielding a further 15.3 g of crystalline product, mp 82°–84° C., containing 95% by weight of a 1:1 mixture of the 1R cis S- and 1S cis R-isomers.

The filtrate from this second step was concentrated to 25 ml and treated as in the second step to give a further 7.7 g of crystalline product, mp 83°–84° C., containing 95% by weight of a 1:1 mixture of the 1R cis S- and 1S cis R-isomers.

Thus in three treatment steps a 95% pure 1:1 mixture of 1R cis S- and 1S cis R-isomers of the starting material was obtained in 90% yield.

EXAMPLE 3

118.7 g of a mixture of cis-isomers of α-cyano-3-phenoxylbenzyl 3-(2,2-dichlorovinyl)-2,2-dimethylcyclopropane carboxylate containing 69% by weight of the 1S cis S- and 1R cis R-isomers and 31% by weight of the 1R cis S- and 1S cis R-isomers was dissolved in 236 ml of triethylamine and the solution was subject to treatment similar to Example 2. 61.7 g of crystalline product, mp 81°–83° C., containing 95% by weight of a 1:1 mixture of the 1R cis S- and 1S cis R-isomers was obtained.

The filtrate was concentrated to 70 ml and treated as in the second step of Example 2 to give a further 24.4 g of crystalline product, mp 76°–80° C., containing 90% by weight of a 1:1 mixture of the 1R cis S- and 1S cis R-isomers.

Thus in two treatment steps 73% by weight of the starting material was obtained in the form of a greater than 90% pure 1:1 mixture of the 1R cis S- and 1S cis R-isomers.

EXAMPLE 4

906 g of a mixture of cis-isomers of α-cyano-3-phenoxybenzyl 3-(2,2-dichlorovinyl)-2,2-dimethylcyclopropane carboxylate containing 42% by weight of the 1S cis S- and 1R cis R-isomers and 58% by weight of the 1R cis S and 1S cis R isomers was dissolved in 1812 ml of triethylamine with heating to 70° C. The resulting solution was filtered through a No. 3 porosity sinter and was allowed to cool whilst being stirred with a polytetrafluoroethylene-bladed paddle. At 26° C. the solution was seeded with a few crystals of a 1:1 mixture of 1R cis S- and 1S cis R-isomers of α-cyano-3-phenoxybenzyl 3-(2,2-dichlorovinyl)-2,2-dimethylcyclopropane carboxylate. Stirring was continued for two days, the solution reaching an end temperature of 20° C. The solid material which had separated out was filtered off, sucked dry, washed once with 500 ml of 60–80 petroleum ether at −10° C. and dried to constant weight in a vacuum oven at ambient temperature, to give 638 g of crystalline product, mp 82°–84° C., which was shown by high performance liquid chromatography to contain 94% by weight of a 1:1 mixture of the 1R cis S- and 1S cis R-isomers of the starting material.

The filtrate was concentrated to 800 ml, heated to 60° C., allowed to cool with stirring and seeded at 30° C. with a few crystals of a 1:1 mixture of the 1R cis S- and 1S cis R-isomers of α-cyano-3-phenoxybenzyl 3-(2,2-dichlorovinyl)-2,2-dimethylcyclopropane carboxylate. Stirring was continued for three days, the solution reaching an end temperature of 23° C. The solid material which had separated out was filtered off, sucked dry, washed once with 200 ml of triethylamine at −10° C. and once with 200 ml of 60–80 petroleum ether at −10° C. and dried as above to give a further 178 g of crystalline product, mp 83°–85° C., containing 98% by weight of a 1:1 mixture of the 1R cis S- and 1S cis R isomers.

The filtrate from this second step was concentrated to 200 ml and treated similarly as in the second step, but with stirring for five days, to give further 51 g of crystalline product, mp 82°–84° C., containing 92% by weight of 1:1 mixture of the 1R cis S- and 1S cis R-isomers.

Thus in three treatment steps a 94% pure 1:1 mixture of 1R cis S- and 1S cis R-isomers of the starting material was obtained in greater than 95% yield.

EXAMPLE 5

For comparison purposes several different organic amines were used as base-solvent systems in the following test procedure. 5.0 g of a mixture of cis-isomers of α-cyano-3-phenoxybenzyl 3-(2,2-dichlorovinyl)-2,2-dimethylcyclopropane carboxylate, in which by weight ratio of 1S cis S- and 1R cis R-isomers to 1R cis S- and 1S cis R-isomers was 2:1, was dissolved in 10 ml of the organic amine with heating (to not more than 60° C.). The resulting solution was allowed to cool to ambient temperature with stirring, and was seeded with a few crystals of a 1:1 mixture of 1R cis S- and 1S cis R-isomers of α-cyano-3-phenoxybenzyl 3-(2,2-dichlorovinyl)-2,2-dimethylcyclopropane carboxylate. Stirring was continued overnight and the solution was then subjected to further treatment, analysis, etc. as appropriate. Results are given in Table I following. Analyses of solutions and end products were effected by high performance liquid chromatography. In cases where crystallisation did not occur at ambient temperature the solutions were cooled to −10° C. in order to attempt to achieve crystallisation.

TABLE I

| Test No. | Organic Amine | Comments |
|---|---|---|
| i | triethylamine | Slow crystallisation. After two days of stirring, precipitate was filtered and dried to give 2.0 g of 98% pure 1:1 mixture of 1R cis S— and 1S cis R isomers. Filtrate contained substantially racemic mixture of cis-isomers. No decomposition of starting material detectable. |
| ii | diisopropylamine | Slow crystallisation. After two days of stirring, precipitate was filtered and dried to give 2.0 g of a 98% pure 1:1 mixture of 1R cis S— and 1S cis R— isomers. Filtrate contained substantially racemic mixture of cis-isomers. About 5% decomposition of starting material detected. |
| iii | tri-n-propylamine | Rapid crystallisation. After stirring over weekend, precipitate was filtered, washed with 60–80 petroleum ether and dried to give 3.3 g of crystalline material having substantially the same composition as the starting material. |
| iv | tri-n-butylamine | Slow crystallisation. After stirring over weekend, precipitate was filtered, washed with 60–80 petroleum ether and dried to give 3.9 g of crystalline material having substantially the same composition as the starting material. |
| v | diethylamine | No crystallisation. Stirred for two hours at −10° C., still no crystallisation. About 20% decomposition of starting material detected after one day. |
| vi | n-hexylamine | No crystallisation. Rapid decomposition of starting material had occurred. |
| vii | n-butylmethylamine | No crystallisation, even after five days. About 50% decomposition of starting material detected after one day. Over 90% decomposition detected after nine days. |
| viii | N—cyclohexylmethylamine | No crystallisation even after three days. About 50% decomposition of starting material detected after three days. |
| ix | N—cyclohexylisopropylamine | No crystallisation after three days. Very little decomposition of starting material. Solution contained substantially racemic mixture of cis-isomers. |
| x | ethyldiisopropylamine | Rapid crystallisation. After stirring over weekend precipitate was filtered and dried to give 3.0 g of crystalline material having substantially the same composition as the |

TABLE I-continued

| Test No. | Organic Amine | Comments |
|---|---|---|
| xi | N,N—dimethyl-aniline | starting material. No crystallisation. |
| xii | 2,6-lutidine | No crystallisation. No decomposition of starting material detected. Isomer composition of starting material unchanged. |

EXAMPLE 6

Experiments to assess the effect of the presence of water in the base-solvent system were effected by the procedure of Example 5. In each case the base-solvent was triethylamine. Results are given in Table 2 following.

TABLE II

| Test No. | % water in triethylamine (w/w) | Comments |
|---|---|---|
| i | 0.10 | see Table I |
| ii | 2 | Slow crystallisation. After two days of stirring, precipitate was filtered and dried to give 0.9 g of a 98% pure 1:1 mixture of 1R cis S— and 1S cis R— isomers Filtrate contained substantially racemic mixture of cis-isomers |
| iii | 5 | No crystallisation even after five days |

EXAMPLE 7

3125 g of a freshly prepared racemic mixture of cis-isomers of α-cyano-3-phenoxybutylbenzyl 3-(2,2-dichlorovinyl)-2,2-dimethylcyclopropane carboxylate, purity 96.3% by weight, in the form of a yellow oil was dissolved in 4.65 liters of triethylamine at ambient temperature. The solution was seeded with a few crystals of a 1:1 mixture of 1R cis S- and 1S cis R-isomers of α-cyano-3-phenoxybenzyl 3-(2,2-dichlorovinyl)-2,2-dimethylcyclopropane carboxylate and was stirred for 24 hours at 15° C. The precipitate which crystallised out was filtered off, washed with 750 ml of cold triethylamine and with 1 liter of 60–80 petroleum ether and dried to give 1738 g of colourless crystals mp 81°–83° C.

The filtrate was evaporated to about 1400 g of an oil which was dissolved in 2 liters of triethylamine at ambient temperature. The solution was seeded as above and stirred for 48 hours at 15° C. The precipitate which crystallised out was filtered off, washed with 500 ml of cold triethylamine and with 500 ml of 60–80 petroleum ether and dried to give 864 g of colourless crystals mp 81.5°–83.5° C.

The filtrate was evaporated at about 511 g of an orange oil which was dissolved in 750 ml of triethylamine at ambient temperature. Treatment as above, with stirring at 15° C. for 48 hours, yielded a further 96 g of colourless crystals, mp 82.5°–84° C.

The combined crystalline product (overall yield 2698 g, 86% by weight) was shown by high performance liquid chromatography to contain 94% by weight of a 1:1 mixture of the 1R cis S- and 1S cis R-isomers of α-cyano-3-phenoxybenzyl 3-(2,2-dichlorovinyl)-3,3-dimethylcyclopropane carboxylate.

We claim:

1. A process for preparing a 1:1 mixture of 1R cis S-isomers and 1S cis R-isomers substantially free of 1S cis S-isomers and 1R cis R-isomers of a compound of formula

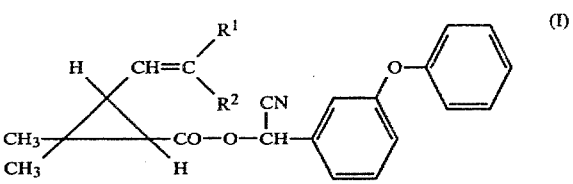

wherein $R^1$ and $R^2$ are selected from the group consisting of chlorine, bromine and methyl, which process comprises:
   dissolving a mixture of 1S cis S-isomers and 1R cis R-isomers of the compound of formula I, in an organic amine base containing from 5 to 7 carbon atoms and is a secondary amine containing two branched alkyl groups or a tertiary amine; and
   crystallizing out from the resulting solution of cis-isomers of formula I in the organic amine base a 1:1 mixture of the 1R cis S-isomers and 1S cis R-isomers substantially free of 1S cis S-isomers and 1R cis R-isomers.

2. A process according to claim 1 wherein $R^1$ and $R^2$ are both chlorine.

3. A process according to claim 1 wherein the organic amine base contains six carbon atoms.

4. A process according to claim 1, wherein dissolution in the organic amine base and crystallization from the resulting solution are effected under substantially anhydrous conditions.

5. A process according to claim 1, wherein crystallization from the solution is effected at about −0° to about 20° C.

6. The process of claim 4, wherein water comprises less than about 0.5 percent by weight of the organic amine base.

7. The process of claim 1, wherein the mixture of 1S cis S-isomers and 1R cis R-isomers of the compound of formula I is dissolved in the organic amine base in the presence of 1R cis S-isomers and 1S cis R-isomers.

8. The process of claim 1, wherein the organic amine base is a tertiary amine.

9. The process of claim 8, wherein the tertiary amine is triethylamine.

10. The process of claim 1, wherein the organic amine base is a secondary amine having two branched alkyl groups.

11. The process of claim 10, wherein the secondary amine having two branched alkyl groups is diisopropyl-amine.

12. The process of claim 1, wherein the mixture of isomers of the compound of formula I is dissolved in the organic amine base at an elevated temperature of about 50° to about 80° C.

13. The process of claim 1, wherein the 1S cis R-isomers and 1R cis S-isomers crystallized are removed from solution to permit the formation of additional 1S cis R-isomers and 1R cis S-isomers.

14. A process for preparing a 1:1 mixture of 1R cis S-isomers and 1S cis R-isomers of a compound of formula

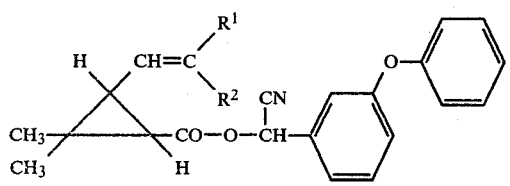

wherein $R^1$ and $R^2$ are selected from the group consisting of chlorine, bromine and methyl, which process comprises:

dissolving a mixture of 1S cis S-isomers and 1R cis R-isomers of the compound of formula I in triethylamine in the presence of 1R cis S-isomers and 1S cis R-isomers of the compound of formula I at a temperature of about 60° to about 70° C.;

said triethylamine containing less than about 0.5 percent water by weight; and crystallizing out from the resulting solution of cis-isomers of formula I in the triethylamine at a temperature of about 0° to about 20° C. a 1:1 mixture of the 1R cis S-isomers and 1S cis R-isomers substantially free of 1S cis S-isomers and 1R cis R-isomers.

* * * * *